United States Patent
Sen et al.

(10) Patent No.: US 6,593,130 B1
(45) Date of Patent: Jul. 15, 2003

(54) METHOD AND APPARATUS FOR EX VIVO AND IN VIVO CELLULAR ELECTROPORATION OF GENE PROTEIN OR DRUG THERAPY

(75) Inventors: Luyi Sen, Stevenson Ranch, CA (US); Guanggen Cui, Stevenson Ranch, CA (US); Jack W. Judy, Los Angeles, CA (US); Hillel Laks, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/549,904

(22) Filed: Apr. 14, 2000

Related U.S. Application Data

(60) Provisional application No. 60/129,817, filed on Apr. 16, 1999.

(51) Int. Cl.[7] .................................................. C12M 1/42
(52) U.S. Cl. ............................. 435/285.2; 435/173.5; 604/21
(58) Field of Search ............................... 435/43, 173.5, 435/285.2; 604/20, 21

(56) References Cited

U.S. PATENT DOCUMENTS

| | | | |
|---|---|---|---|
| 5,273,525 A | | 12/1993 | Hofmann et al. ............. 604/21 |
| 5,304,120 A | | 4/1994 | Crandell et al. ............... 604/82 |
| 5,507,724 A | | 4/1996 | Hofmann et al. ............. 604/53 |
| 5,795,755 A | * | 8/1998 | Lemelson ................ 435/173.5 |
| 6,010,573 A | * | 1/2000 | Bowlin ........................ 118/620 |
| 6,041,252 A | * | 3/2000 | Walker et al. ................ 604/20 |
| 6,090,617 A | * | 7/2000 | Meserol .................... 435/285.2 |

FOREIGN PATENT DOCUMENTS

| | | |
|---|---|---|
| WO | WO/9116945 | 11/1991 |
| WO | WO/9604955 | 2/1996 |
| WO | WO/9843702 | 10/1998 |

* cited by examiner

*Primary Examiner*—David A. Redding
(74) *Attorney, Agent, or Firm*—Daniel L. Dawes; Myers Dawes Andras & Sherman LLP

(57) ABSTRACT

An array is placed in contact with or close proximity with an organ or tissue surface to cause electroporation for gene, protein, drug delivery in both ex vivo and in vivo applications. A low DC voltage with a short pulse duration, and long burst pulse is applied to the array. A long rest period is provided between pulse bursts to allow for cell recovery. To enable the application of a low voltage shock in a large organ with same transfection efficiency, four gene, protein and drug delivery systems are illustrated.

38 Claims, 12 Drawing Sheets

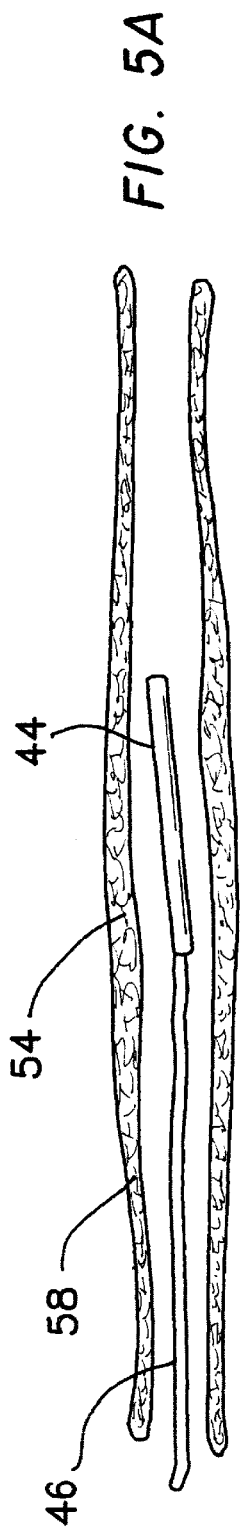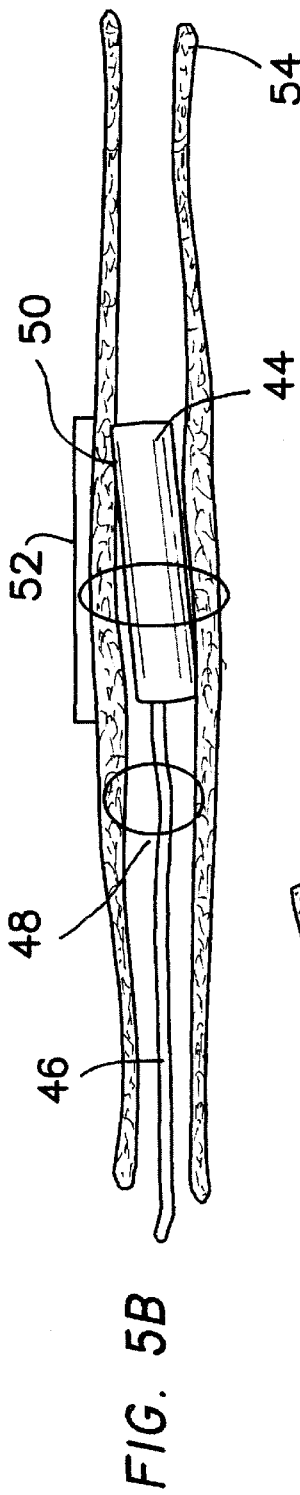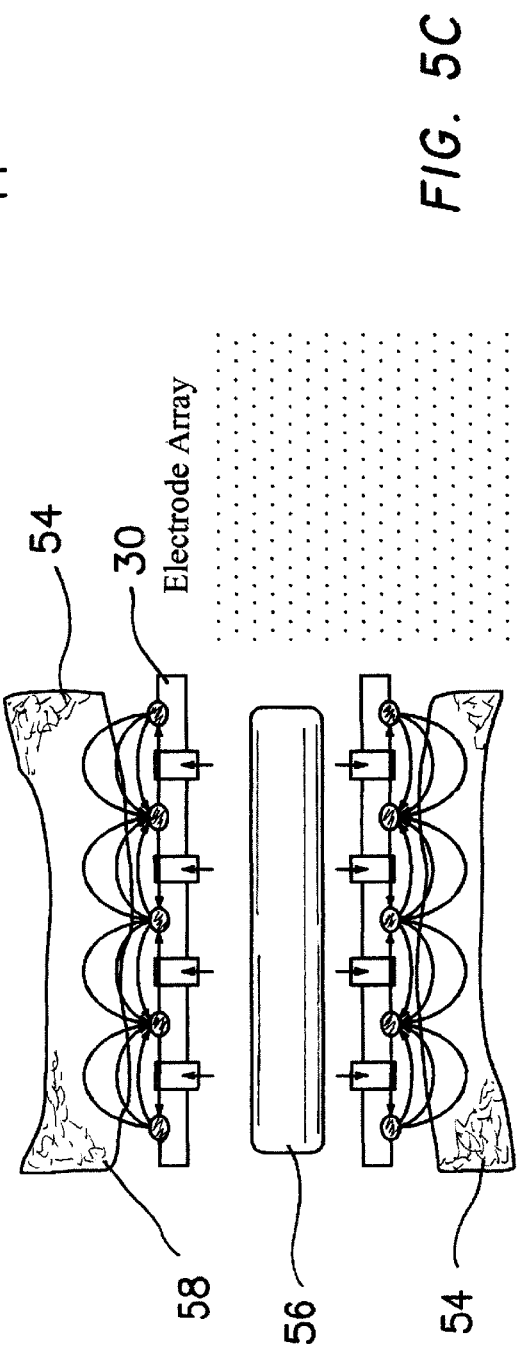
FIG. 5A
FIG. 5B
FIG. 5C

LIPOSOME-MEDIATED

ELECTROPORATION-MEDIATED

METHOD AND APPARATUS FOR EX VIVO AND IN VIVO CELLULAR ELECTROPORATION OF GENE PROTEIN OR DRUG THERAPY

RELATED APPLICATION

The application is related to provisional patent application Ser. No. 60/129,817, filed on Apr. 16, 1999, which is incorporated herein by reference.

BACKGROUND OF THE INVENTION

1. Field of the Invention

The invention relates to the field of cellular electroporation for gene, protein, or drug therapy and in particular to the application of gene-therapy for the rejection of heart or organ transplantation, cardiovascular disease and cancer in any organ.

2. Description of the Prior Art

Electroporation is a technique involving the application of short duration, high intensity electric field pulses to cells or tissue. The electrical stimulus causes membrane destabilization and the subsequent formation of nanometersized pores. In this permeabilized state, the membrane can allow passage of DNA, enzymes, antibodies and other macromolecules into the cell. Electroporation holds potential not only in gene therapy, but also in other areas such as transdermal drug delivery and enhanced chemotherapy. Since the early 1980s, electroporation has been used as a research tool for introducing DNA, RNA, proteins, other macromolecules, liposomes, latex beads, or whole virus particles into living cells. Electroporation efficiently introduces foreign genes into living cells, but the use of this technique had been restricted to suspensions of cultured cells only, since the electric pulse are administered with cuvette type electrodes.

Electroporation is commonly used for in vitro gene transfection of cell lines and primary cultures, but limited work has been reported in tissue. In one study, electroporation-mediated gene transfer was demonstrated in rat brain tumor tissue. Plasmid DNA was injected intra-arterially immediately following electroporation of the tissue. Three days-after shock treatment expression of the lacZ gene or the human monocyte chemoattractant protein-1 (MCP-1) gene was detected in electroporated tumor tissue between the two electrodes, but not in adjacent tissue. Electroporation has also been used as a tissue-targeted method of gene delivery in rat liver tissue. This study showed that the transfer of genetic markers β-glactosidase (β-gal) and luciferase resulted in maximal expression at 48 hr, with about 30–40% of the electroporated cells expressing β-gal, and luciferase activities reaching peak levels of about 2500 μg/mg of tissue.

In another study, electroporation of early chicken embryos was compared to two other transfection methods: microparticle bombardment and lipovection. Of the three transfection techniques, electroporation yielded the strongest intensity of gene expression and extended to the largest area of the embryo. Most recently, an electroporation catheter has been used for delivery heparin to the rabbit arterial wall, and significantly increased the drug delivery efficiency.

Electric pulses with moderate electric field intensity can cause temporary cell membrane permeabilization (cell discharge), which may then lead to rapid genetic transformation and manipulation in wide variety of cell types including bacteria, yeasts, animal and human cells, and so forth. On the other hand, electric pulses with high electric field intensity can cause permanent cell membrane breakdown (cell lysis). According all the knowledge available now, the voltage applied to any tissue must be as high as 100–200 V/cm. if it is to be used on large animal or a human organ, such as human heart, it must be several kV. It will cause enormous tissue damage. Therefore, this technique is still not applicable for clinical use.

Electroporation is commonly used for in vitro gene transfection of cell lines and primary cultures, but limited work has been reported in organized tissue. According to the theory in in vitro study, the membrane voltage, $V_m$, at different loci on phospholipid bilayer spheres during exposure in a homogenous electric field of duration t, can be calculated from $$V_m = 1.5\ r_c\ E\ \cos\alpha[1-\exp(-t/\tau)] \qquad (1)$$

where E is the electric field strength, $r_c$ is the cell radius, $\alpha$ is the angle relative to the direction of the electric field, and $\tau$ is the capacitive-resistive time constant. Pore-formation will result at those spherical coordinates exposed to a maximal potential difference, which is at the poles facing the electrodes ($\cos\alpha=1$ for $\alpha=0$; $\cos\alpha=-1$ for $\alpha=\pi$). Generally, electric field strengths on the order of 1 to 1.5 kV/cm for duration of a few μs to a few ms are sufficient to cause transient permeabilization in 10-μm outer-diameter spherical cells. A recent study shows that isolated mitochondria, because of their correspondingly smaller size, require 7- to 10-fold higher electric field strengths to incorporate a 7.2-kilobase plasmid DNA. Mitochondrial outer-membrane fusion at lower electric field strengths of=2.5 kV/cm also has been observed.

According to three most recent studies of gene delivery to rat liver and embryonic chick heart, the voltage applied to any tissue must be as high as 100–200 V/cm. However, this is much lower than the theoretical level calibrated from equation (1). For gene delivery in an organ the magnitude of voltage can be much lower than that for cell suspension. However, more accurate calibration is not available. Even according this prior art information, if one wishes to use electroporation on a large animal or human organ, such as human heart, it must be at lest several kV. Such voltage levels will cause enormous tissue damage. Therefore, this technique is still not applicable for use in any large animal or human organs.

What is needed is some means of increasing electroporation without causing tissue damage.

BRIEF SUMMARY OF THE INVENTION

The invention is an apparatus for electroporation of biological cells. The invention comprises a perfusion medium in which the biological cells are disposed, typically in the form of organized tissue or a whole organ. The tissue or organ may be either in vivo or ex vivo. A source of a low voltage, pulsed, DC electric gradient field is established across the biological cells, tissue or organ. A source of genes, proteins, and/or drugs to be delivered through perfusion of the organ, then be transferred into and from the perfusion medium into the biological cells is also provided by conventional means.

The source of a low voltage, pulsed, DC electric gradient field is a conductive array disposable in proximity or contact to the biological cells, tissue or organ. In the case where the tissue or organ has a cavity the array is disposed in and conformable to the interior walls of the cavity. In the case of a solid organ, the array is conformable to the external wall of the organ. In the case where the tissue or organ is ex vivo the array is in contact with an exterior surface of the tissue or organ.

In one embodiment the conductive array may be comprised of a first part disposable in contact with a cavity defined in the tissue or organ, and a second part disposable in contact with the exterior surface of the tissue or organ. Opposite polarities of voltage are applied to the first and second parts of the conductive array. The conductive array is comprised of a flexible mesh conformable to the cavity.

In another embodiment the conductive array is comprised of a first plurality of electrodes having a first polarity and a second plurality of electrodes having a second polarity. The low voltage, pulsed, DC electric gradient field is established between the first plurality of electrodes and the second plurality of electrodes.

The source of a low voltage, pulsed, DC electric gradient field provides a high frequency pulsed DC field applied to the biological cells at a group repetition rate. Preferably the low voltage, pulsed, DC electric gradient field provides a voltage gradient across the biological cells of 0.1 to 10 V/cm. In the illustrated embodiment the source of a low voltage, pulsed, DC electric gradient field provides a pulse of DC voltage of approximately 1–5 ms long at approximately 500 Hz with a 50% duty cycle. The low voltage, pulsed, DC electric gradient field is provided in a burst of pulses of DC voltage followed by a rest period of the order of several seconds to 10 minutes, typically of the order of 5 seconds. There are typically 5 to 10 short pulses in every burst.

The apparatus further comprises an inflatable balloon disposed within the conductive array.

In another embodiment the conductive array is a pair of opposed plates between which the biological cells, tissue or organ are disposed. In the case where the tissue defines a lumen, the conductive array is a cylindrical mesh inflatable within the lumen. The cylindrical mesh is comprised of a plurality of separate electrodes provided in two sets with opposing polarities.

For a solid organ, such as the prostate, liver, and kidney, ex vivo, the gene, protein and drug delivered to the organ through an artery or vein, then a conductive array mesh in contact with the organ provides the organ with negative charge, and a central wire will be placed in the main artery is provided with a positive charge. The burst pulses of DC voltage are then applied to the mesh.

The invention is also defined as a method for electroporation of biological cells comprising the steps of disposing the biological cells, tissue or organs in a perfusion medium, and establishing a low voltage, pulsed, DC electric gradient field across the biological cells. Genes, proteins, and/or drugs are transferred into and then from the perfusion medium into the biological cells, tissue or organs. As discussed above the low voltage, pulsed, DC electric gradient field is applied as a high frequency pulsed DC field to the biological cells, tissue or organs at a group repetition rate. The low voltage, pulsed, DC electric gradient field is applied as a voltage gradient across the biological cells of 0.1 to 10 V/cm. For example, in one embodiment it is applied as a pulse of DC voltage of approximately 1 ms long pulse at approximately 500 Hz with approximately a 50% duty cycle. The low voltage, pulsed, DC electric gradient field is applied as a burst of pulses of DC voltage followed by a rest period of the order of several seconds to 10 minutes. The burst of pulses of DC voltage is applied as a burst of pulses of the order of 0.1–2 seconds in duration.

The invention now having been briefly summarized, it is illustrated in the following drawings wherein like elements are referenced by like numerals.

BRIEF DESCRIPTION OF THE DRAWINGS

FIG. 5a is a diagrammatic side cross-sectional view of a catheter being inserted into a perfusion zone with the array in a collapsed condition.

FIG. 5b is a diagrammatic side cross-sectional view of a catheter in a perfusion zone after the array has been expanded by a concentric balloon and after upstream and downstream balloons have been deployed.

FIG. 5c is a diagrammatic side cross-sectional view of the catheter shown in enlarged scale depicting the fringing field from the electrodes provided by inflated the array.

Figure 1A:
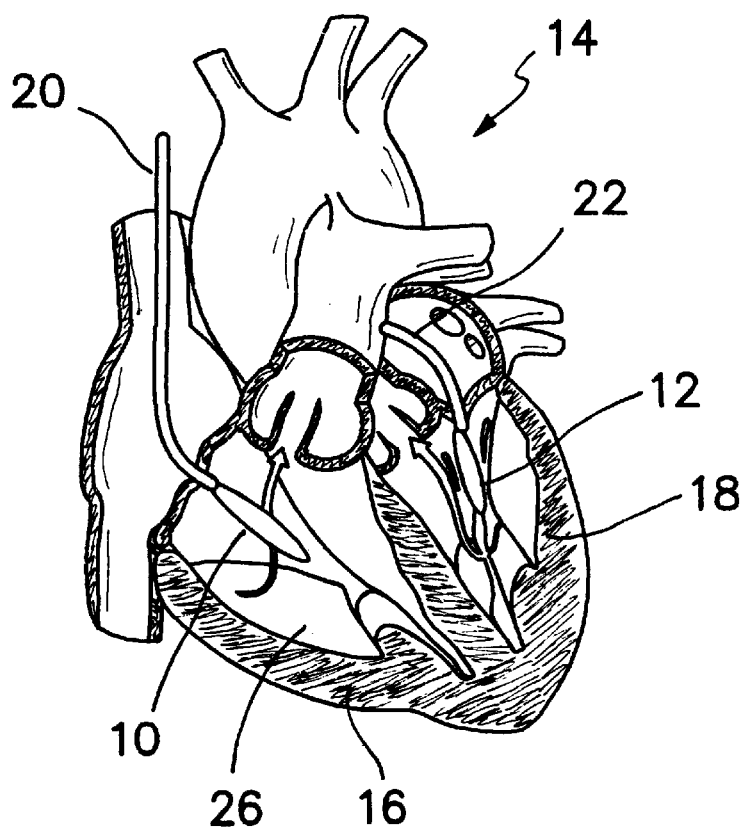
FIG. 1a is a diagrammatic cross-sectional view of a human heart in which uninflated arrays have been placed in the ventricles.

The invention and its various embodiments can now be understood by turning to the following detailed description of the preferred embodiments.

DETAILED DESCRIPTION OF THE PREFERRED EMBODIMENTS

Under physiological conditions of harvest and implantation, gene transfer can result in the expression of either a reporter or an immunologically relevant protein in a functioning heterotopical transplanted heart. The concept of intracoronary delivery of recombinant genes is also part of the invention. Initially, intracoronary infusion of cytomegalovirus-promoter luciferase deoxyribonucleic plasmids in cationic liposomes proved to be an effective method of gene delivery. Ex vivo and in vivo gene delivery methodologies using intracoronary catheterization have been established according to the invention and the potential utility of adenovirus-mediated and liposome-mediated reporter gene and therapeutic genes transfer and its efficacy, therapeutic effects, and adverse effects of the invention has been evaluated.

Nonviral gene transfer has significant advantages because of its low toxicity and lack any immune response—allowing it to be used for repetitive gene therapy. However, a serious challenge is the low gene transfer efficiency. What has been developed is liposome-mediated gene transfer strategies for ex vivo and in vivo gene therapy. What is disclosed below are new electrode configurations and catheters for ex vivo and in vivo gene transfer, tests for their efficiency and adverse effects, and an investigation of their feasibility for use with entire human organs.

The ex vivo and in vivo electroporation systems of the invention are disclosed. The optimized electrical parameters can be determined systematically by examining the feasibility, efficacy and adverse effects of various gene therapy in acute and chronic rejection of animal heart transplant models. Finally, the applicability of the ex vivo and in vivo electroporational gene transfer methodology are also determined in a human.

The invention thus includes not only developing and optimizing these new therapeutic approaches, but also a basic understanding of the mechanism of electric field application for gene therapy, and the evaluation of the feasibility, efficacy and adverse effects of this technology.

The invention establishes the concept and applicable methodology for facility of gene, protein or drug therapy targeting in organ and tissue of large animal and human ex vivo and in vivo for using new electroporation strategies. The gene delivery systems are used for transferring any therapeutic gene, protein or drugs to the isolated organ and tissue ex vivo, vessels and tissue in vivo such as heart, lung, liver kidney, etc. ex vivo.

The illustrated embodiments of the invention are shown in four applications:

1) gene, protein and drug delivery in vivo to an isolated organ;
2) gene, protein and drug delivery ex vivo to isolated tissue;
3) gene, protein and drug delivery in vivo to an organ; and
4) gene, protein and drug delivery in vivo to a vessel wall.

The concept of this invention is to introduce a strategy for electro permiablization in gene, protein, drug targeting in human organ ex vivo and in vivo, that is to use low voltage, short pulse duration, and long burst pulse applications. To enable the application of a low voltage shock in a large organ with same transfection efficiency, four gene, protein and drug delivery systems are illustrated below.

The invention is directed to an electroporation system which applies a high frequency pulsed, low DC voltage for gene transfer. Four illustrated gene delivery systems are described below which apply a low voltage shock to a large organ with high transfection efficiency ex vivo and in vivo. The four electroporation-mediated gene targeting systems include: (i) ex vivo gene transfer in large animal and human hearts, (ii) in vivo gene transfer in a large animal and human hearts, (iii) ex vivo gene transfer in coronary arterial wall of large animal and human, and (iv) in vivo gene transfer in coronary arterial wall of large animal and human. It is to be expressly understood that the type of applications to which the invention may be applied is not limited to these four, but may include gene, protein and drug delivery in vivo and ex vivo to any type of biological target.

What is provided is a low voltage, short duration and high frequency DC pulse applied in a burst-stop form or with a group repetition to heart 14 or vessel 40, 54. As depicted by the wave diagram of FIGS. 9 1 ms pulses of DC voltage 0.1 to 10 V/cm DC are applied to electrode arrays 10, 12, 34, 36 at a frequency of 400 to 600 Hz. The ranges recited are merely illustrative and other values for each of the signal parameters may be chosen consistent with the teachings of the invention. Using the ex vivo electroporation-mediated gene transfer systems of the invention, a voltage gradient of 1–5 V/cm across the wall of heart 14 is sufficient to induce about a 50 fold increase in IL-10 gene expression in whole rabbit heart. This is higher than any previously reported gene transfer methodology, which include any known virus-mediated gene transfer. The magnitude, distribution, dose-dependence and time-dependence of gene overexpression can also be varied to further optimize the total gene transfer as shown in FIGS. 9a–12b.

The gene overexpression induced by electroporation-mediated gene transfer in a rabbit heart ex vivo and in vivo using 10 mV/cm to 100 V/cm pulsed voltage gradients is described as follows. The pulse duration in vitro and in vivo in previous studies has been reported over a very wide variable range, from 10 $\mu$s to 500 ms. Even in two studies of organ gene transfer, in embryonic chick heart the pulse duration was 10 ms, but in rat liver, it was 25–99 ms. In our preliminary study, the pulse width was 1 ms (500 Hz pulse rate at a 50% duty cycle). A pulsed frequency is used to demonstrate a high-resolution technique to alter the biochemical content for organelles in situ, based on permeabilization of phospholipid bilayer membranes by pulsed electric fields (electroporation). The highest gene expression efficiency is obtained by using a high frequency pulse, namely 400–600 Hz.

Figure 9A:
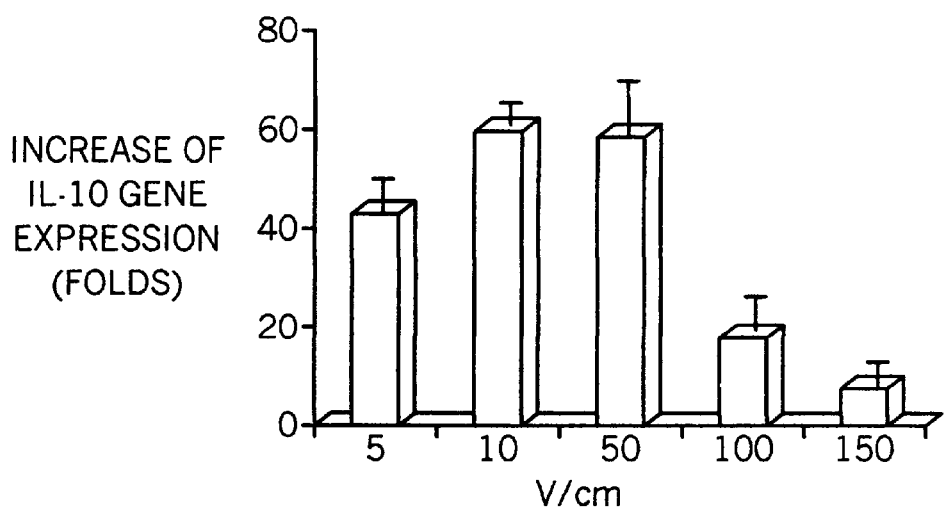
FIG. 9a is a bar graph illustrating the gene expression induced by different strengths of electrical field.
Figure 9B:
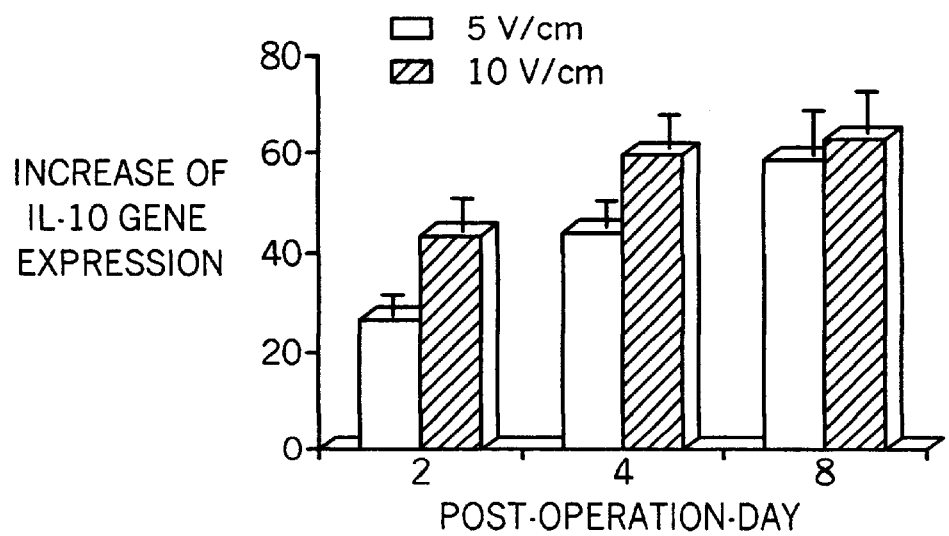
FIG. 9b is a bar graph comparing temporal gene transfer facilitated by electroporation at 5V/cm and 10 V/cm.
Figure 10A:
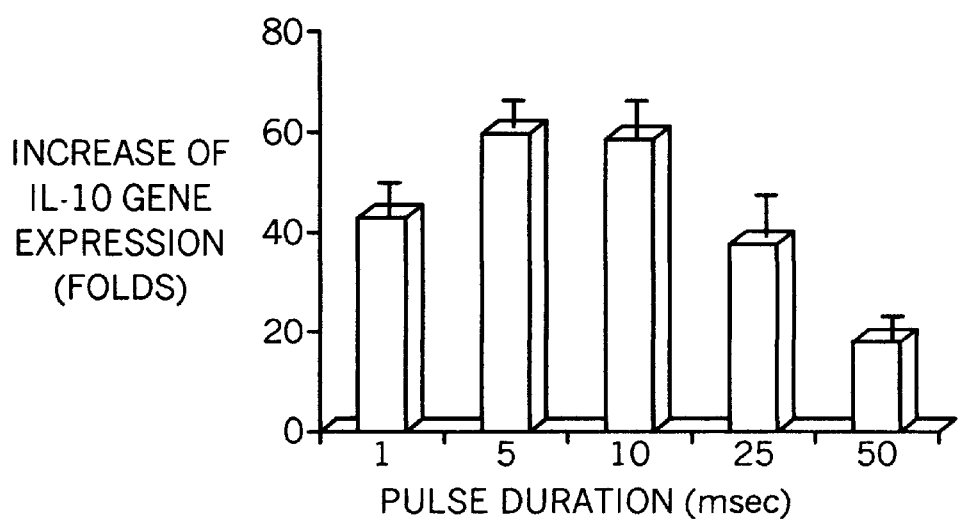
FIG. 10a is a bar graph illustrating the efficiency of gene transfer facilitated by electroporation by different pulse durations.
Figure 10B:
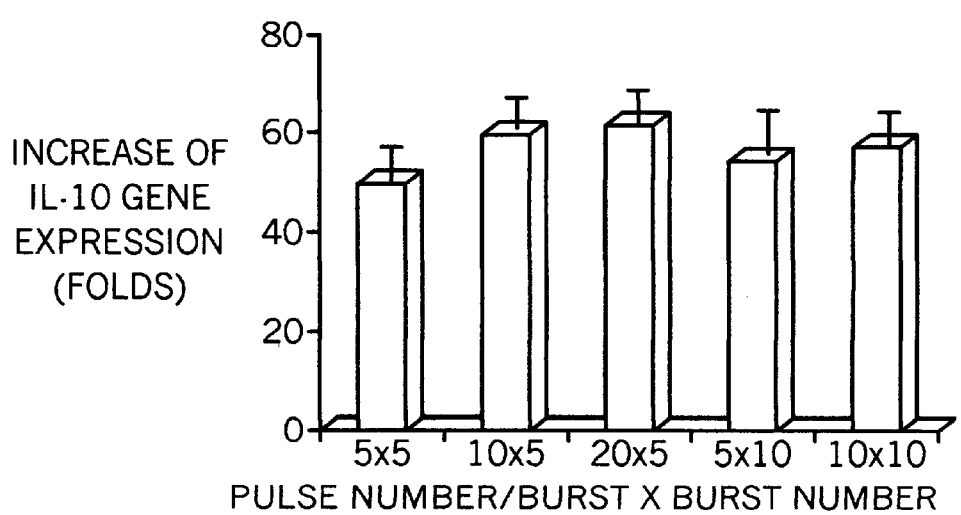
FIG. 10b is a bar graph illustrating the efficiency of gene transfer facilitated by different combinations of the number of pulses per burst and the number of bursts.
Figure 11A:
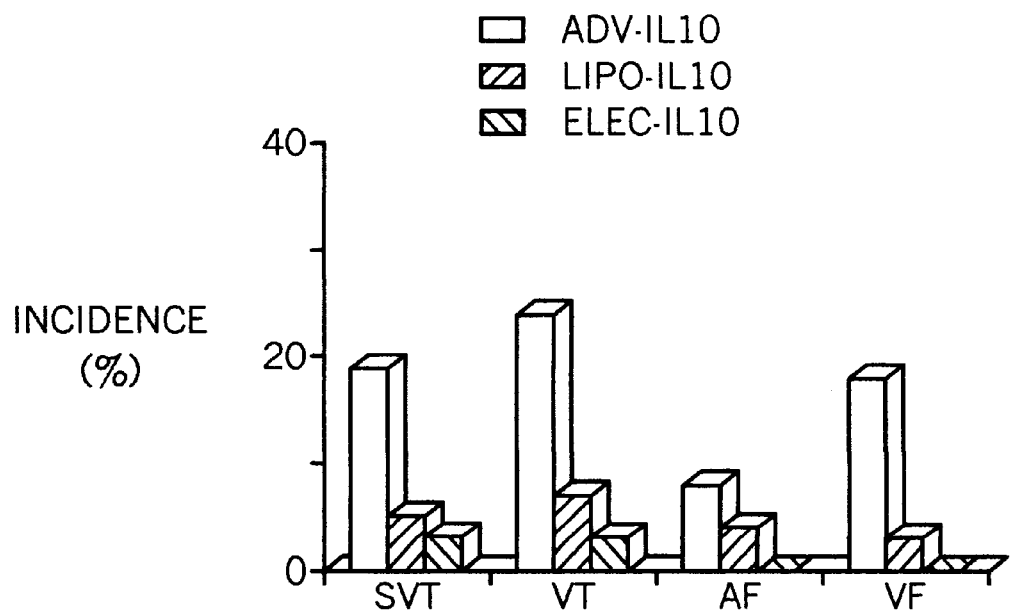
FIG. 11a is a bar graph illustrating the arrhythmogenic effects of adenovirus and liposome on electroporation.
Figure 11B:
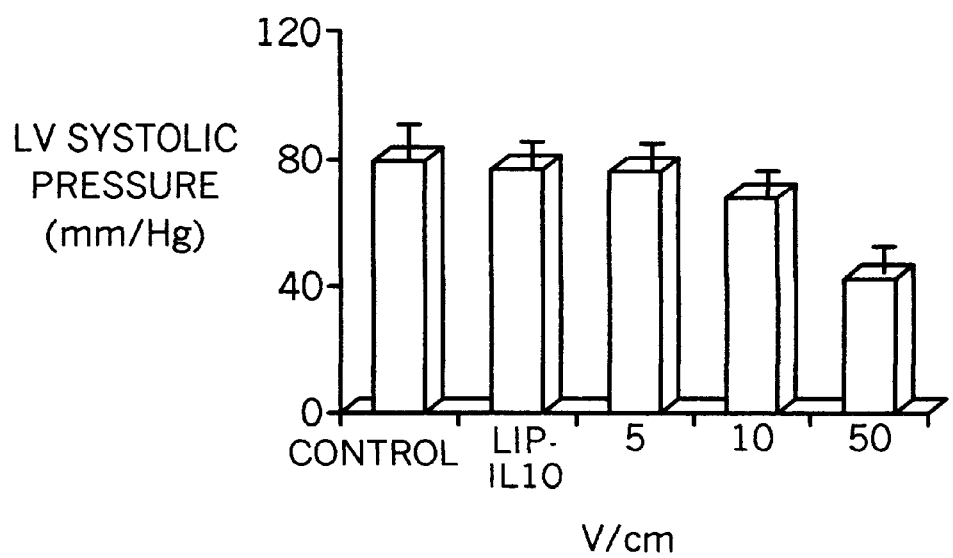
FIG. 11b is a bar graph illustrating the effects of different strengths of electroporation effects on the left ventricular systolic pressure compared with that in liposome mediated gene transfer.
Figure 12A:
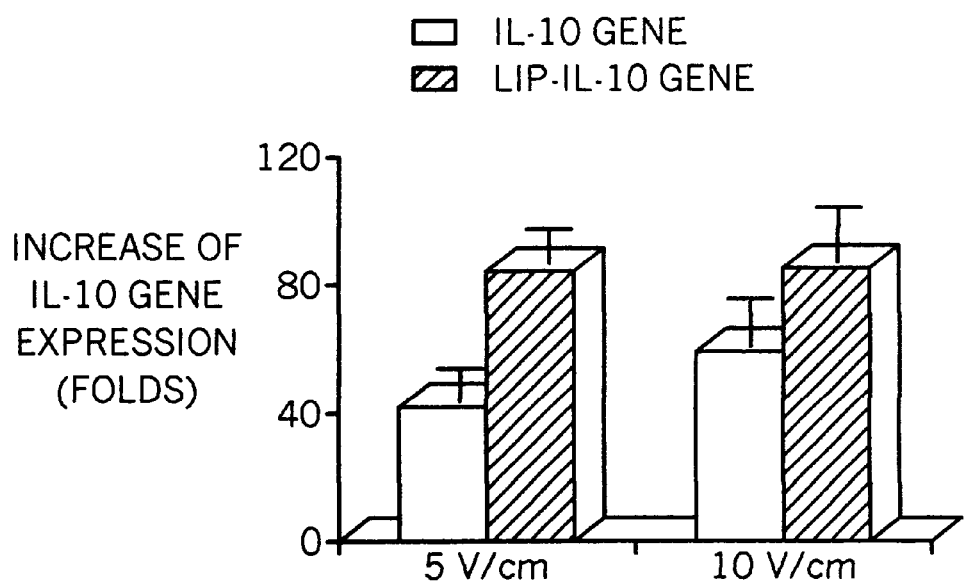
FIG. 12a is a bar graph illustrating the efficiency of gene transfer due to electroporation in the gene and liposome-gene complex.
Figure 12B:
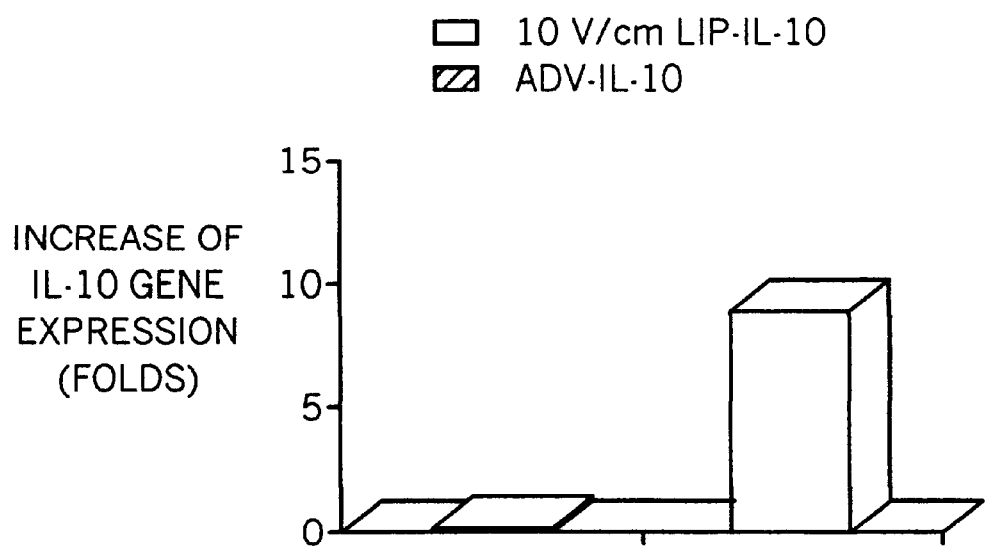
FIG. 12b is a bar graph illustrating the efficiency of gene transfer induced by electroporation observed 6 hours after gene transfer but not in adenovirus-induced gene transfer.

In the illustrated embodiment, after the gene reaches the cell membrane, a burst of pulses for 0.1–1 s as shown in FIG. 9 is applied to let the gene pass through the membrane into the cytosol. This minimizes time for the cell membrane's "break down". After these gene particles enter into the cell during the burst time, the cell is provided for substantially longer time to reestablish the balance, namely about 5 s. During this resting period, new gene particles will reach the cell membrane and touch the cell membrane. The burst is then repeated and an addition perfusion performed. The number of perfusion cycles thus performed may be in the range of 5 to 20.

Consider a first embodiment of FIGS. 1a–2b where an isolated organ 14 is provided with gene, protein and drug delivery ex vivo. In the following, the organ will be shown as a heart, but it must be understood to refer to any organ, or tissue and in particular an organ with a cavity. This embodiment illustrates gene, protein, drug delivery when organ 14 is isolated from body as part of an organ transplant procedure. Organ 14 is surrounded by an open, conductive noninsulated mesh 24 to which the voltage is applied while the agent or drug is infused into the local area through mesh 24 as shown in FIG. 2a and in cross-sectional view in FIG. 2b. In heart 14 a conductive mesh is applied both inside the heart cavity in the form of arrays 10 and 12 as shown in FIGS. 1a and 1b and outside the heart in the form of array 24. FIG. 1a shows arrays 10 and 12 inserted into heart 14 while noninflated. FIG. 1b shows arrays 10 and 12 inserted into heart 14 and inflated in order to place arrays 10 and 12 into contact or close proximity with the heart wall. In an organ without a large cavity, the opposing electrode array (not shown) is placed on the infusion catheter which is disposed in the organ in place of arrays 10 and 12.

The important issues to address when attempting to achieve uniform electroporation on biological tissues or entire organs, while in in vivo and ex vivo situations, include (1) maintaining adequate perfusion of the gene and (2) insuring that the applied electric field pulses are of sufficient, but not of an excessive, magnitude and duration. In order to establish a particular electric gradient field strength, the separation between the electrodes must be known. Theoretical analysis and computer simulations of electric gradient field distributions are used to characterize the specific the electrode designs employed, which will be dependent on the geometry of the array. In addition to creating analytical models for the performance of each electrode design, advanced engineering computer-aided design tools (CAD) solve for finite element method (FEM) solutions for the electric field distribution. A uniform electric field is preferred, since a nonuniform field, such as the much higher field near sharp points, can lead to cell, tissue, or organ damage or death.

Figure 1B:
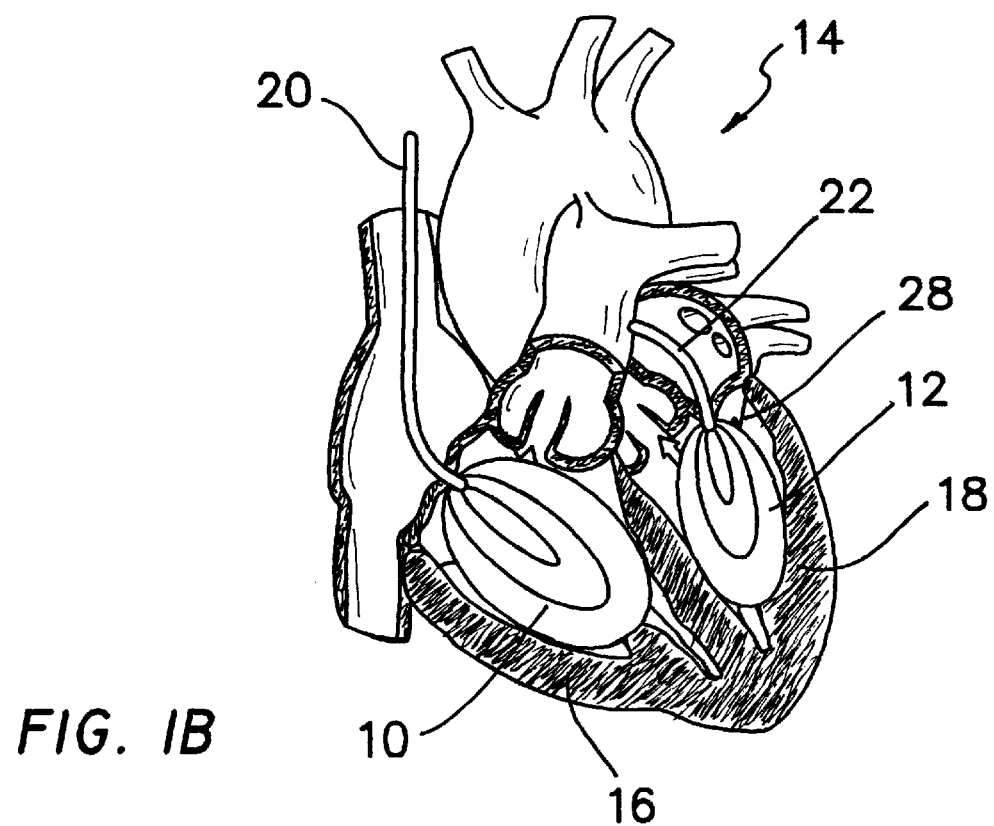
FIG. 1b is a diagrammatic cross-sectional view of a human heart in which the arrays have been inflated in the ventricles.
Figure 2A:
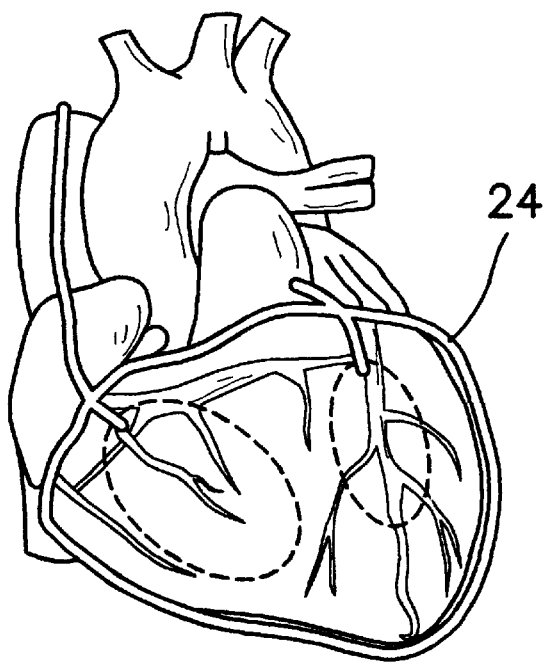
FIG. 2a is a diagrammatic exterior view of a human heart around which an array has been placed.
Figure 2B:
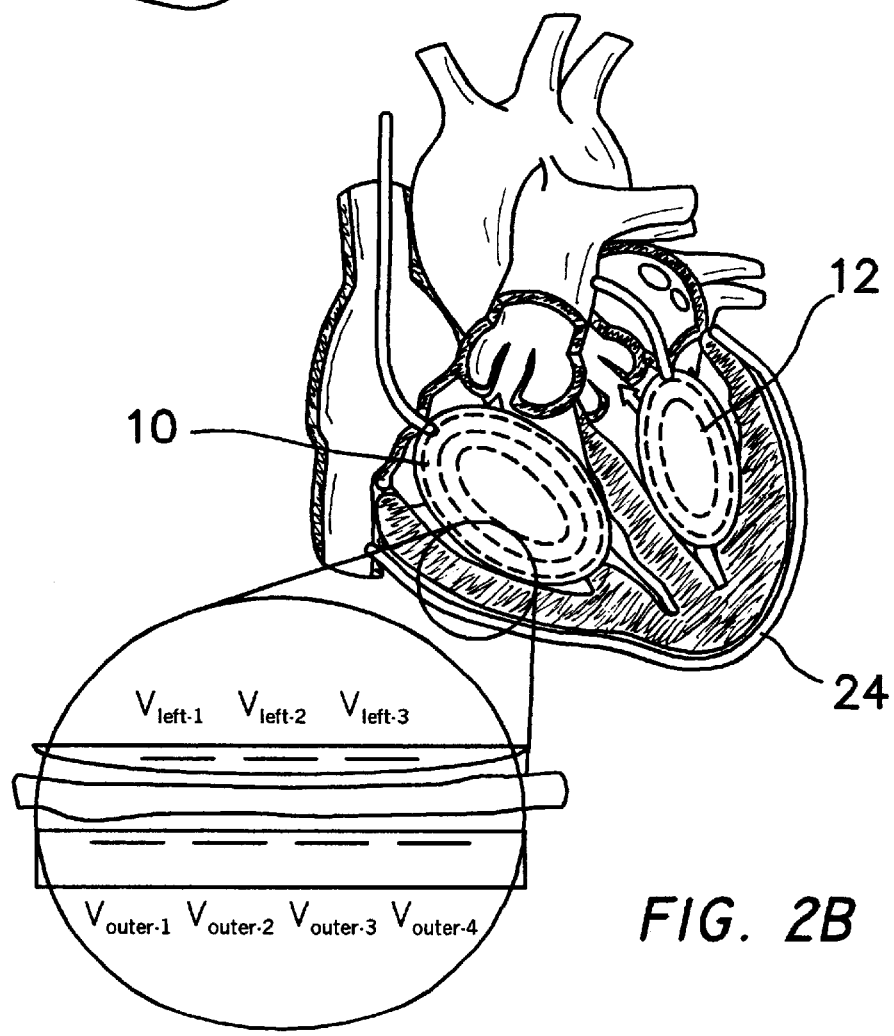
FIG. 2b is a diagrammatic cross-sectional view of the human heart of FIG. 2a in which inflated arrays have been placed in the ventricles.

For example, consider an ex vivo gene transfer in a heart 14. In order to achieve uniform electroporation-enhanced gene transfer to the entire human heart, special attention must be paid to the electrode configuration. One pair of simple parallel-plate conductors placed across the entire heart (i.e., from one side to the other side) will require a very large voltage to establish the electric field gradient normally associated with electroporation (>100 V/cm). Furthermore, the direction of the applied field relative to the surface of the heart will not be uniform. The electrode arrays of the invention comprise two major components: (1) a pair of dense, expandable, open electrode arrays 10 and 12 that can be inserted inside heart 14, e.g. one in each ventricular chamber 16 and 18, with catheters 20 and 22 respectively as diagrammatically shown in FIG. 1a in an uninflated condition, and in an inflated condition as shown in FIG. 1b; and (2) a dense electrode array 24 fitted over the exterior of heart 14 as shown in FIGS. 2a and 2b. The advantages of this design are that the distance between the electrode arrays 10 and 12 inside heart 14 and electrode array 24 placed on the outer surface of the heart 14 will be minimized to only the thickness of the intervening heart wall which is approximately 6 mm, in a relaxed state.

Perfusion of a gene-carrying medium, such as liposome-IL-10 gene complex can be accomplished by using one of the conventional catheters perfusing through coronary arteries. An expansible lantern of stainless steel is inserted into an uninsulated, stainless steel woven mesh sock plated with platinum which comprises array 10 or 12 which is made from a mesh. Array 10 or 12 is fabricated from stainless steel wire, so that it is highly flexible. The entire array is provided with the same voltage and there is no separate electrodes provided since the array as a whole acts as a single electrode. Alternatively, array 10 and 12 may be attached at one or more points to the outside of the expansible balloon on which it is carried.

In addition, by selectively tailoring the voltage applied to each individual electrode in array 10 or 12 or set of electrodes in array 10 or 12, a relatively uniform electrical field can be induced throughout the entire heart despite variations in wall thickness, thereby promoting uniform gene transfer. In this embodiment array 10 and 12 are comprised of copper wires forming separate circuits in which portions of the insulation has been removed to expose the wire to form an active electrode. As many different circuits may be formed in the array as desired in order to realize the object electric field gradient strength from the array when inflated. The insulated wires are attached to each other by soldering at the wire cross-over points or are woven together to form the mesh which comprises the array Voltage differences between the interior and exterior electrode arrays 10, 12 on one hand and 24 on the other will treat exterior walls 26 of heart 14. Voltage differences between the two interior electrode arrays 10 and 12 will treat interior walls 28 of heart 14.

Figure 4A:
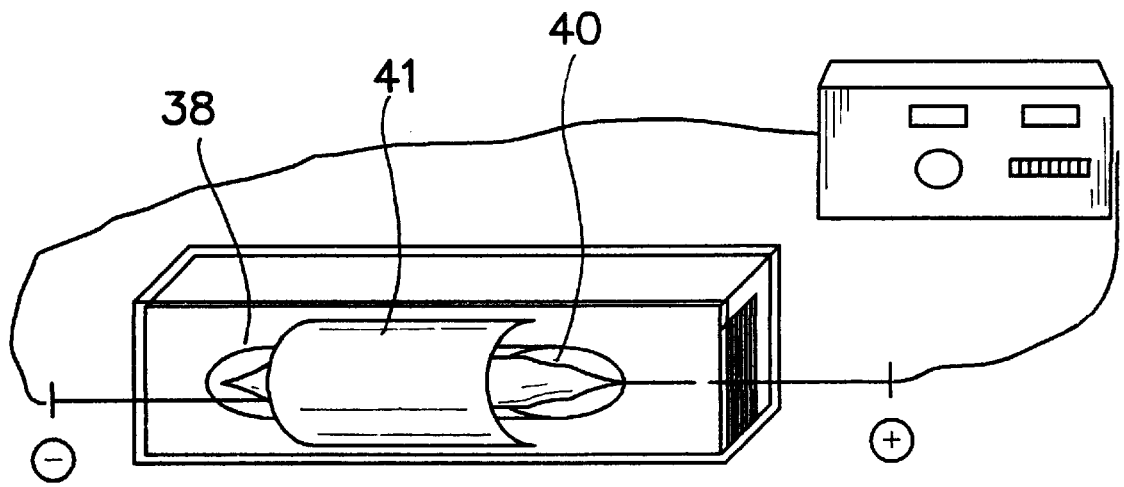
FIG. 4a is a diagrammatic side cross-sectional view of an ex vivo embodiment of the invention in which tissue is being perfused.

Turn now to gene, protein and drug delivery ex vivo to an isolated tissue, which need not be an organ. This embodiment is for gene, protein, drug delivery when the tissue is isolated from the body such as in vein or arterial graft for coronary artery bypass surgery (CABG) in coronary artery disease. The target tissue 40 is disposed between a flexible plate and a balloon 38 immersed in medium 42 through Which the electroporating field is applied as shown in FIG. 4a. The deflated platinum plated balloon was inserted into the vessel. A stainless steel plate, 0.5 mm thick covered and contacted the outside of the vessel. A maximum voltage gradient of about 10 V/cm is applied across them. Medium 42 is a physiologic buffer, such as normal saline and includes the gene, protein, or drug in solution or suspension for delivery.

Now consider an in vivo gene transfer in heart 14. The challenges associated with in vivo gene transfer to heart 14 are considerably more difficult than those encountered in the ex vivo case. For example, in order to insure adequate perfusion of the gene-carrying medium throughout in vivo heart 14, perfusion catheters need to be inserted into both the left and right coronary arteries. In addition, an electrode array 24 cannot be placed on the exterior of heart 14. This last limitation necessitates an electrode array design and operation different from that shown in FIGS. 1a–2b.

Figure 3A:
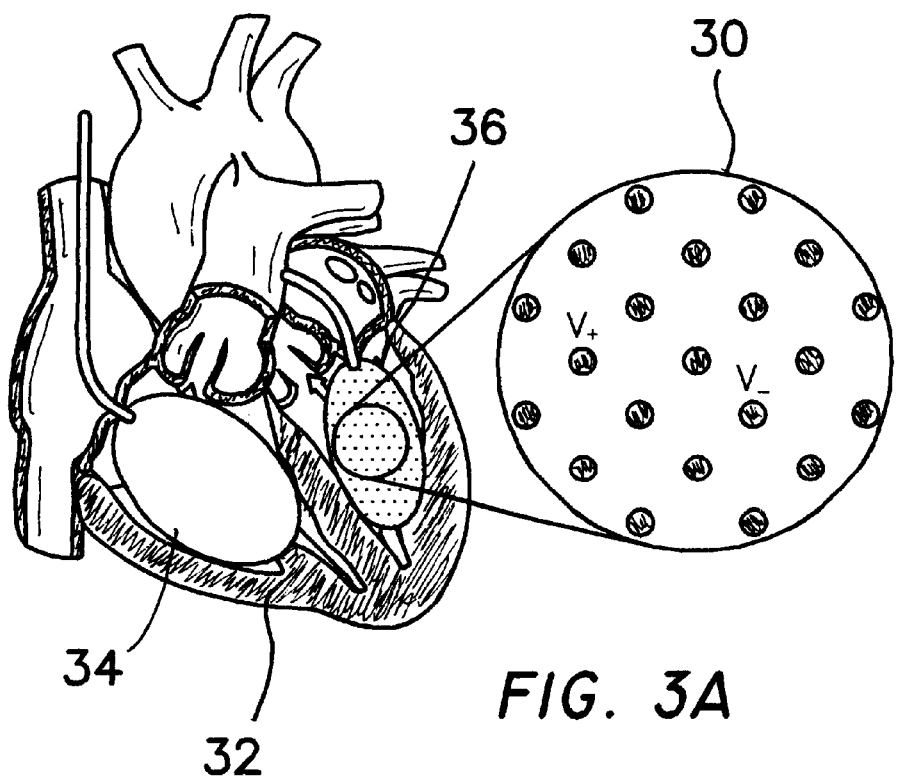
FIG. 3a is a diagrammatic cross-sectional view of the human heart in vivo of in which inflated arrays have been placed in the ventricles.
Figure 3B:
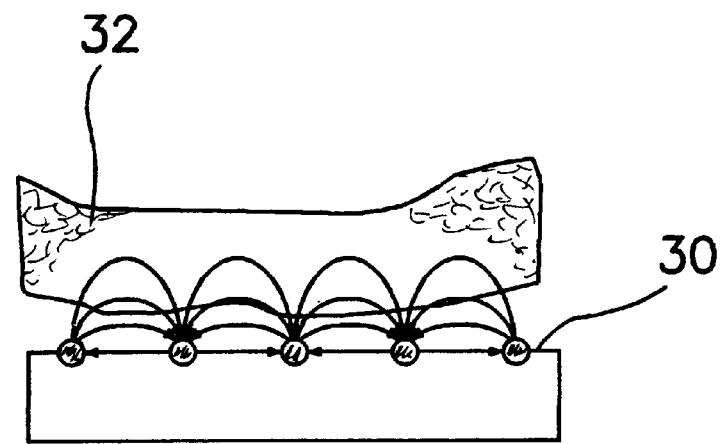
FIG. 3b is a diagrammatic side cross-sectional view of an portion of the array-to-heart wall contact of FIG. 3a shown in enlarged scale.

As shown in FIG. 3a, again the open electrode arrays 34 and 36 are inserted into heart 14 with catheters 20 and 22 respectively and then inflated with balloons as before to establish intimate contact or proximity between electrodes 30 of arrays 34 and 36 and interior heart wall 32. Electrode arrays 34 and 36 in this case are each comprised of an array of discrete electrodes 30 with alternating potentials. Thus at least two separate circuits are provided in arrays 34 and 36, namely one for the positive potential and one for the negative potential. The fringing electric fields between electrodes 30 of different potentials that result when a voltage is applied will be used to initiate electroporation as diagrammatically depicted in FIG. 3b. Electrodes 30 are formed with a spherical copper body which was plated with platinum and are interconnected in their respective circuit by flexible insulated copper wires.

Figure 4B:
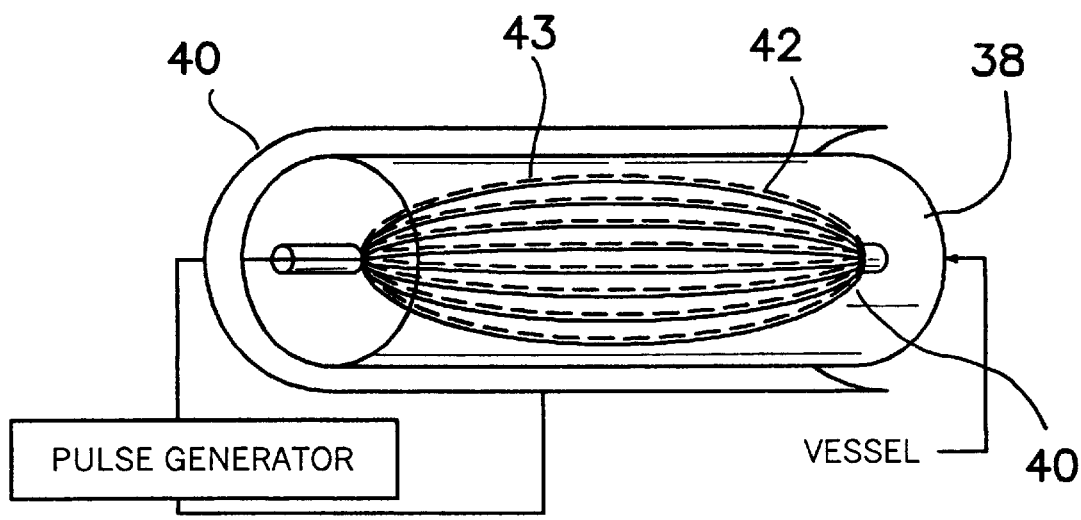
FIG. 4b is a diagrammatic view of an in vivo embodiment of the invention in which tissue is being perfused with an endoscope.

Consider further gene, protein and drug delivery in vivo to an organ. The method is the same as for perfusion into heart 14 described in connection with FIGS. 1a–4, except the mesh socks are replaced by a mesh pad 45 applied to the tissue place through an endoscope as shown in FIG. 4b. Consider the delivery of gene, protein and drug delivery to a solid organ ex vivo. The mesh pad 45 was applied to the outside of the organ. The gene, protein or drug was delivered through an artery or vein. A central wire in the artery or arteries served as the positively charged electrode.

Consider the delivery of gene, protein and drug delivery to a vessel wall in vivo. The challenges associated with the in vivo gene transfer to the coronary arterial wall are very similar to those associated with the in vivo gene transfer to heart 14. Consequentially, the solutions will also be very similar. A significant difference is the method of perfusion. In this case, the gene-carrying media will be perfused down the catheter and out through a permeable electrode array that is inflated by a balloon on the inside (see FIGS. 6a–6d).

The mesh electrodes, forming a square or hexagonal mesh pattern of an alternating array of polarized electrodes 30 similar in concept to the embodiment of FIGS. 3 and 4, are disposed in a cylindrical mesh array 44 on the outside of a catheter 46, which is ideally provided with upstream and downstream balloons 48 and 50 to temporarily block agent infusion to the electroporation zone 52 in a vessel or lumen 54. FIG. 5a is a diagrammatic side cross-sectional view of catheter 46 being inserted into a perfusion zone 52 with array 44 in a collapsed condition. FIG. 5b is a diagrammatic side cross-sectional view of catheter 46 in a perfusion zone 52 after array 44 has been expanded by a concentric balloon and after upstream and downstream balloons 48 and 50 have been deployed. FIG. 5c is a diagrammatic side cross-sectional view of catheter 46 shown in enlarged scale depicting the fringing field from electrodes 30 provided by inflated array 44. An inflation balloon 56 is provided on catheter 46 to expand array 44 to bring insulated electrodes 30 into close proximity to walls 58 of lumen 54.

Some examples will now be provided of gene, protein and drug therapy for preventing acute arid chronic allograft rejection. It must be expressly understood that the application of the invention is not limited to the examples which are chosen for illustration, but include any biological electroporation consistent with the teachings of the invention. Acute and chronic allograft rejection is still the major problem in any organ transplantation. In organ transplantation, there is great opportunity for apply a therapeutic gene, protein, drug, such as immunosuppressive genes, proteins, and drugs, to prevent allograft rejection. The embodiment described above in connection with FIGS. 1a, 1b and 2 is used to exam the preventive effect of IL-10 in the acute allograft rejection in heart transplantation in rabbit. See FIGS. 8–9.

Gene, protein arid drug therapy for vein and arterial graft is also illustrated. Restenosis is still the major problem for CABG. Most recent study has show that the immunosuppressive cytokine has preventive effect for the restenosis. The embodiment of FIG. 3a described above is used to testing the IL-10 gene effect on the vein graft restenosis in rabbit model. There is also a potential for treatment of some autoimmuno vessel disease. The tpA gene is being tested on the same model. There is also a potential for delivering heparin in the vessel wall for prevent restenosis.

Gene, protein and drug therapy in vivo for preventing arid treatment of allograft rejection, chemotherapy is illustrated by the following. When an organ has been transplanted in situ, the targeting of any therapeutic gene, protein and drug to the allograft with a high concentration and without a systemic effect is ideal. The same is true of chemotherapy. The embodiment described in connection with FIGS. 6a–6d above is used for this application. Percutaneously catheterization and placement of the metal mesh 44 through an endoscope can be used for repeated gene, protein and drug application to the tissue.

Figure 6:
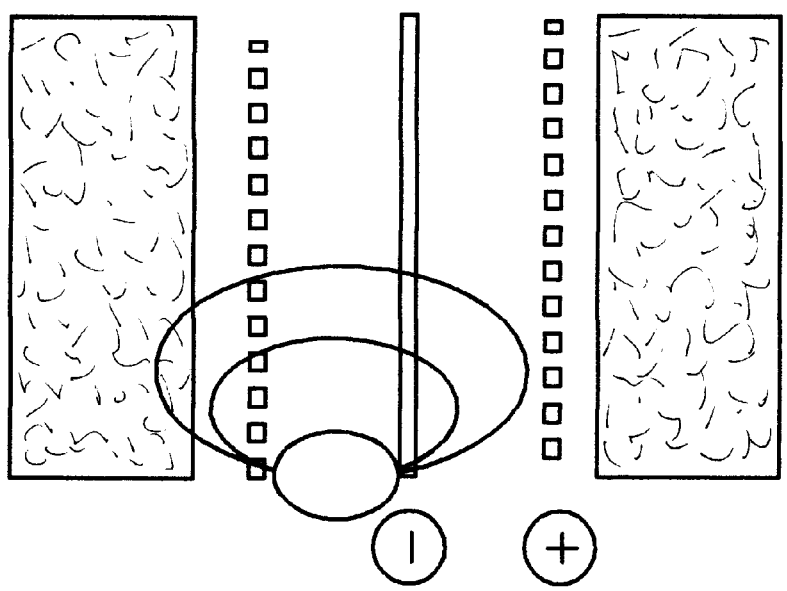
FIG. 6 is a prior art electroporation catheter, which has, a very limited area of tissue which was exposed to the electric field.
Figure 6:
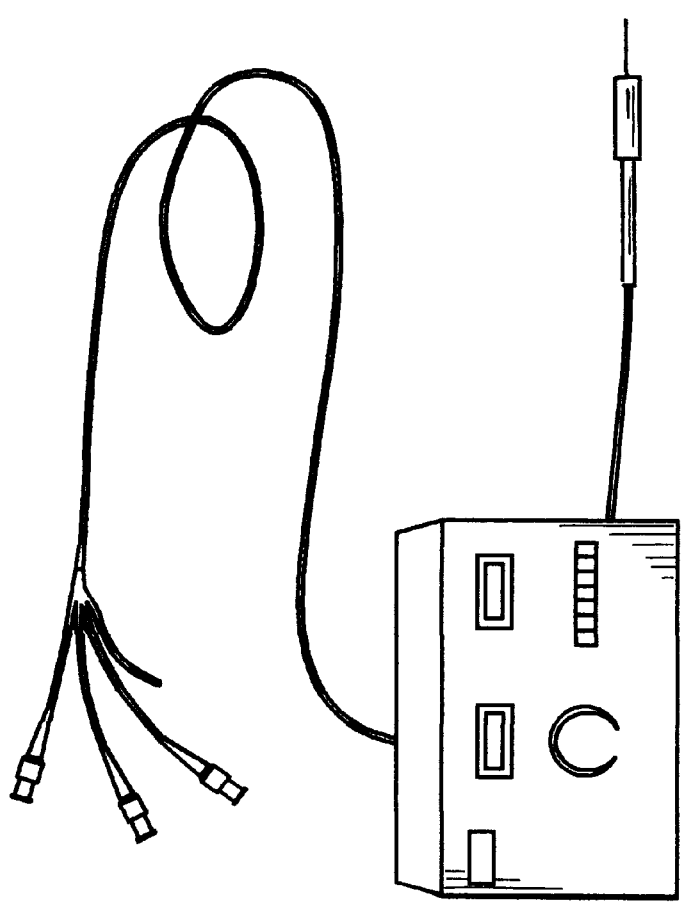

Gene, protein and drug therapy in vivo for any vessel disease, such as coronary artery disease, restenosis, can be provided. A catheter for this purpose has been designed as shown in FIG. 6. The embodiment of FIG. 4b described above uses an electroporation catheter to apply gene, protein and drug for treatment of vessel diseases. It can applied percutaneously and repeatedly. The device included in this invention has a much larger exposed area to the electrical field, therefore, not only does it show better electroporation, but it also greatly reduces the requirements for the strength of the electrical field that is needed for electroporation.

All these techniques can be used for naked DNA, plasmid or liposome-DNA complex. Liposome-DNA complex with the first system in the rabbit heart transplant model has been used to increase the efficiency of IL-10 gene transfer by 20–50% over that realized without electroporation.

This invention opens a new era for the gene, protein and drug targeting in prevention and treatment of large animal and human disease. There does not exist any technique for this purpose which is applicable for human use. The embodiment of FIGS. 6a–6d has four major advantages: 1) low voltage was used for reducing the cell damage; 2) more pulses and longer time can be applied for increasing the gene transfer efficiency; 3) allows the continuing blood flow to prevent the ischemic damage; 4) more even distribution and homogenous strength of electrical field applied on the tissue surface.

The embodiment of FIGS. 1a–4 has been tested using a conventional stimulator on rabbit heart transplant model. The gene transfer efficiency of IL-10 gene and IL-10 gene-liposome complex have been shown increased 20 times for gene and 50% times for DNA-liposome complex.

Electroporation-mediated, IL-10 gene transfer ex vivo in rabbit hearts indicates that adenovirus-mediated gene transfer has high efficiency, but the gene expression is transient. The autoimmune response is responsible for both the tolerance for the further gene transfection and also the excess lymphocytes infiltration, and it may cause the alteration of cardiac function and arrhythmia. The chance of systemic infection is also higher in andenovirus-mediated gene transfer. Liposome-mediated gene transfer is more advantageous. With the new liposome and optimized condition, although the gene transfer efficiency is still lower and initiation is retarded, the efficacy of liposome mediated IL-10 gene transfer for imunosuppression in allograft rejection is same as that in adenovirus-mediated gene transfer. There was no significant adverse effects or toxic effects on heart 14. However, the IL-10 over expression was parallel with the immunosuppression effects, and it was also parallel with the rejection score and cardiac function. It is clear that a higher gene transfer technique is needed.

Figure 7:
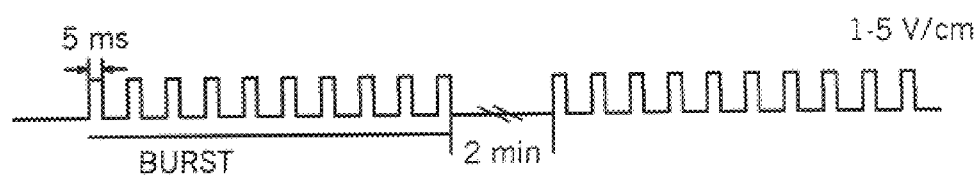
FIG. 7 is a wave diagram showing the low voltage, pulsed DC signal applied to the arrays.
Figure 8A:
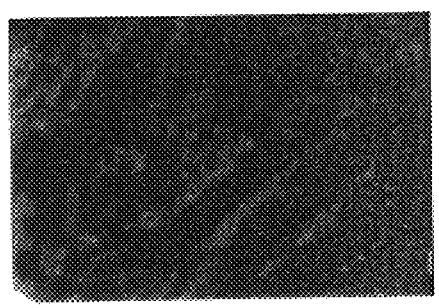
FIG. 8a is an illustration of IL-10 gene expression manifested by immunofluorescence,staining of IL-10 protein in the myocardium treated with IL-10 gene by electroporation compared with and without electroporation.
Figure 8A:
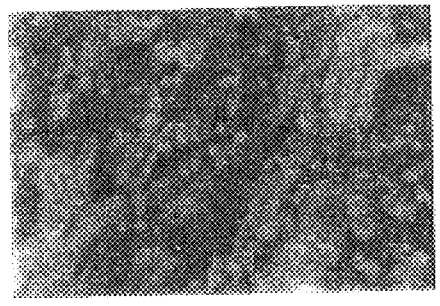
Figure 8B:
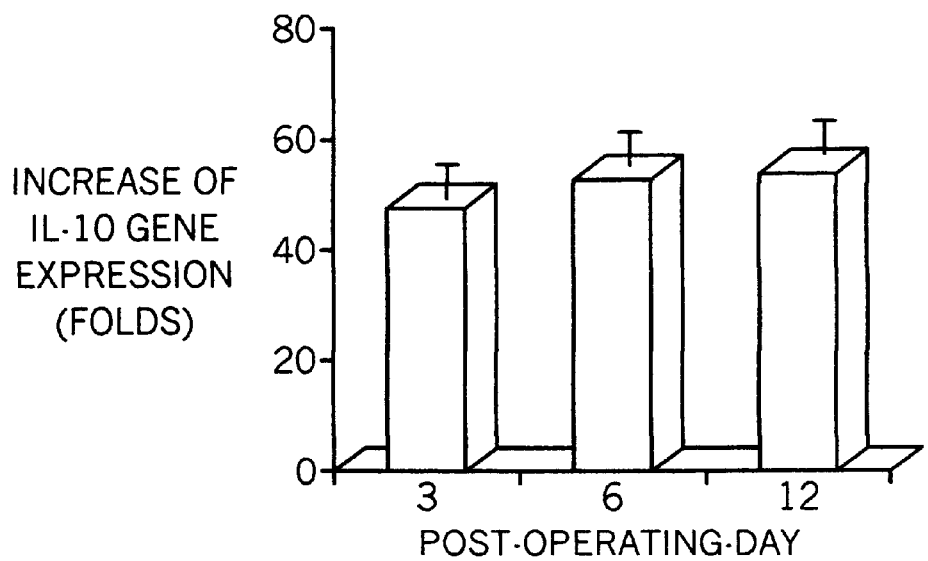
FIG. 8b is a bar graph illustrating the efficacy of gene transfer according to the invention as a function of post-operative time.
Figure 8C:
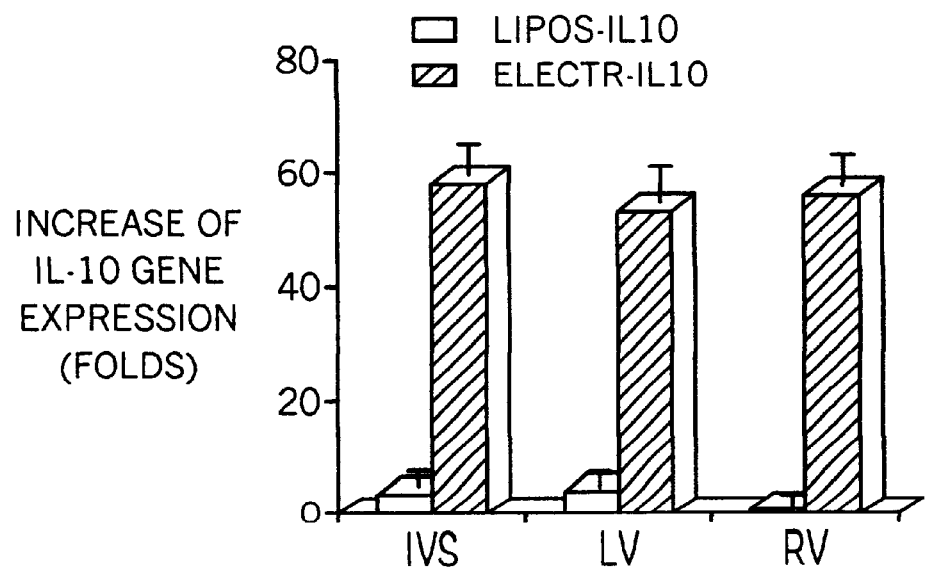
FIG. 8c is a bar graph illustrating the efficacy of gene expressions according to the invention as a function of the gene expression level in the left ventricle, right ventricle and septum, demonstrating the distribution of gene expression.

Using the electroporation method of the invention, the rabbit myocardium can be electropermeablized with low voltage. This method thus abolishes the traditional principle of cuvette set up which was used for in vitro gene transfer and also was used in chick embryo heart gene transfer as most recently reported. It was also greatly improved from the electrical pad system used in rat liver gene transfer as has been previously reported in FEBS 1998; v.425, p436. This method able to homogeneously transfer the genes in to the whole rabbit heart. Moreover, the voltage which was used was only 10 Volts. Compared with that used in chick embryo heart 1.5 kV/cm, it was greatly reduced. As shown in FIG. 7., the electroporation-mediated IL-10 gene transfer caused more than 20 times higher IL-10 overexpression in the rabbit left ventricular myocardium compared with that in liposomemediated gene transfer. The increase of IL-10 mRNA level was reached peak in 3 days after gene transfer as shown in FIG. 7. FIG. 7 is a bar chart of the multiple of IL-10 gene expression as a function of post-operative day of measurement. This increase paralleled with the IL-10 expression at the protein level in gene group. The distribution of the gene expression was much more uniform than that in liposome-mediated gene transfer and adenovirus-mediated gene transfer as shown in FIGS. 8a–c. FIGS. 8b and c is a bar chart of the multiple of IL-10 gene over expression induced by electroporation in comparison with that by liposome, where IVS is intraventricular septum, LV is left ventricle and RV is right ventricle. These results suggest that electroporation mediated gene transfer has high efficiency.

No significant tissue damage induced by electroporation-mediated gene transfer has thus far been observed. The electroporation-mediated gene transfer method of the invention is more promising for the gene delivery in large animal and human.organs than adenovirus- and liposome-mediated gene transfer techniques. It might also become a applicable protein and drug delivery strategy for cardiovascular disease and all other organic disease.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

Although the array has been describe above as being fabricated from discrete wires and electrodes, MEMS fabrication of the array is also expressly contemplated. The techniques and technologies used to produce integrated circuits (ICs) are now being exploited to produce microelectromechanical systems (MEMS) for use in microsensors, microactuators, and microsystems. Although micromachining technologies have been used to realize many commercially successful microsensors and microactuators, the widespread use of MEMS in biomedical applications is just now being investigated and has enormous potential. Magnetic microactuator technology has been developed that can provide long-range and high-force microactuation while immersed in conductive fluids.

To accomplish this, a batch-fabrication process was developed according to the invention in which compatibly integrates ferromagnetic materials into a conventional polysilicon surface-micromachined process used to produce typical MEMS devices. Micromachined probes and electrode arrays are used in (1) neuroscientific instruments and prostheses; (2) miniaturized gas sensor arrays with integrated circuits (ICs) for signal amplification and buffering; and (3) micromachined arrays of electrodes and microfluidic systems for gene-transfer by electroporation at the individual cell and many cell level.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for electroporation of biological cells comprising:
   a perfusion medium in which said biological cells are disposed;
   a source of a low voltage, pulsed, DC electric gradient field established across said biological cells for transferring genes, proteins, or drugs from said perfusion medium into said biological cells;
   a source of genes, proteins, or drugs to be transferred into and then from said perfusion medium into said biological cells; and
   a means for producing a burst of pulses of DC voltage, each of which pulses is followed by a respective rest period during which the cells are permitted to reestablish a balance.

2. The apparatus of claim 1 wherein said source of a low voltage, pulsed, DC electric gradient field is a conductive array disposable in proximity to said biological cells.

3. The apparatus of claim 2 wherein said conductive array is disposable in contact with a tissue comprised of said biological cells.

4. The apparatus of claim 3 wherein said conductive array is disposable in contact with an organ comprised of said tissue.

5. The apparatus of claim 4 wherein said conductive array is disposable in contact with a cavity defined in said organ.

6. The apparatus of claim 4 wherein said conductive array is disposable in contact with an exterior surface of said organ.

7. The apparatus of claim 6 wherein said conductive array is comprised of a first part disposable in contact with a cavity defined in said organ and a second part disposable in contact with said exterior surface of said organ, opposite polarities of voltage being applied to said first and second parts of said conductive array.

8. An apparatus for electroporation of biological cells comprising:
   a perfusion medium in which said biological cells are disposed;

a source of a low voltage, pulsed, DC electric gradient field established across said biological cells for transferring genes, proteins, or drugs from said perfusion medium into said biological cells;

a source of genes, proteins, or drugs to be transferred into and then from said perfusion medium into said biological cells; and wherein said conductive array is comprised of a first plurality of electrodes having a first polarity and a second plurality of electrodes having a second polarity, said low voltage, pulsed, DC electric gradient field being established between said first plurality of electrodes and said second plurality of electrodes.

9. The apparatus of claim 1 wherein said source of a low voltage, pulsed, DC electric gradient field provides a high frequency pulsed DC field applied to said biological cells at a group repetition rate.

10. An apparatus for electroporation of biological cells comprising:

a perfusion medium in which said biological cells are disposed;

a source of a low voltage, pulsed, DC electric gradient field established across said biological cells for transferring genes, proteins, or drugs from said perfusion medium into said biological cells;

a source of genes, proteins, or drugs to be transferred into and then from said perfusion medium into said biological cells; and wherein said source of a low voltage, pulsed, DC electric gradient field provides a voltage gradient across said biological cells of 0.1 to 10 V/cm.

11. The apparatus of claim 9 wherein said source of a low voltage, pulsed, DC electric gradient field provides a pulse of DC voltage of approximately 1 ms long at approximately 500 Hz with a 50% duty cycle.

12. The apparatus of claim 9 wherein said source of a low voltage, pulsed, DC electric gradient field provides a burst of pulses of DC voltage followed by a rest period of the order of several seconds.

13. The apparatus of claim 12 wherein said rest period is of the order of 5 seconds.

14. The apparatus of claim 12 wherein said burst of pulses is of the order of 0.1–2 second.

15. An apparatus for electroporation of biological cells comprising:

a perfusion medium in which said biological cells are disposed;

a source of a low voltage, pulsed, DC electric gradient field established across said biological cells for transferring genes, proteins, or drugs from said perfusion medium into said biological cells;

a source of genes, proteins, or drugs to be transferred into and then from said perfusion medium into said biological cells;

wherein said source of a low voltage, pulsed, DC electric gradient field is a conductive array disposable: in proximity to said biological cells, in contact with a tissue comprised of said biological cells, in contact with an organ comprised of said tissue, in contact with a cavity defined in said organ; and wherein said conductive array is comprised of a flexible mesh conformable to said cavity.

16. The apparatus of claim 15 further comprising an inflatable balloon disposed within said conductive array.

17. An apparatus for electroporation of biological cells comprising:

a perfusion medium in which said biological cells are disposed;

a source of a low voltage, pulsed, DC electric gradient field established across said biological cells for transferring genes, proteins, or drugs from said perfusion medium into said biological cells;

a source of genes, proteins, or drugs to be transferred into and then from said perfusion medium into said biological cells;

wherein said source of a low voltage, pulsed, DC electric gradient field is a conductive array disposable in proximity to said biological cells; and wherein said conductive array is a pair of opposed plates between which said biological cells are disposed.

18. An apparatus for electroporation of biological cells comprising:

a perfusion medium in which said biological cells are disposed;

a source of a low voltage, pulsed, DC electric gradient field established across said biological cells for transferring genes, proteins, or drugs from said perfusion medium into said biological cells; and a source of genes, proteins, or drugs to be transferred into and then from said perfusion medium into said biological cells;

wherein said source of a low voltage, pulsed, DC electric gradient field is a conductive array disposable in proximity to said biological cells and in contact with a tissue comprised of said biological cells; and wherein said tissue defines a lumen and wherein said conductive array is a cylindrical mesh inflatable within said lumen.

19. The apparatus of claim 18 wherein said cylindrical mesh is comprised of a plurality of separate electrodes provided in two sets with opposing polarities.

20. An apparatus for electroporation of biological cells comprising:

a perfusion medium in which said biological cells are disposed;

a source of a low voltage, pulsed, DC electric gradient field established across said-biological cells by two sets of dot electrodes having opposing polarities and defining a surface having a conductive array of said dot electrodes disposable in proximity to said biological cells; and a source of genes, proteins, or drugs to be transferred into and then from said perfusion medium into said biological cells.

21. The apparatus of claim 20 wherein said conductive array is when disposed in proximity to said biological cells openable to thereby permit unimpeded flow of fluid through a central cylindrical lumen defined in said conductive array without interference from obstructions from said conductive array.

22. An apparatus for electroporation of biological cells comprising:

a perfusion medium in which said biological cells are disposed;

a source of a low voltage, pulsed, DC electric gradient field established across said biological cells by a conductive array of dot electrodes defining a surface of said array and disposable in proximity to said biological cells; and a source of genes, proteins, or drugs to be transferred into and then from said perfusion medium into said biological cells;

wherein said conductive array is when disposed in proximity to said biological cells openable to thereby permit unimpeded flow of fluid through a central cylindrical lumen defined in said conductive array without interference from obstructions from said conductive array; and wherein said source of a low voltage, pulsed, DC electric-gradient field comprises a source for pulse repetitions of said low voltage, pulsed, DC electric gradient field.

23. The apparatus of claim 22 wherein said conductive array of dot electrodes are separately addressable so that the magnitude of said DC electric gradient field is independently controllable at each dot electrode.

24. The apparatus of claim 23 wherein said biological cells comprise vascular tissue and further comprising an upstream and downstream blocking balloon to temporarily block body circulation of said genes, proteins, or drugs during perfusion into said vascular tissue.

25. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells wherein said source of a low voltage, pulsed, DC electric gradient field is a conductive array of dot electrodes contoured and disposed in mating contact with an exterior surface of an organ comprised of said biological cells.

26. The apparatus of claim 25 wherein said conductive array is comprised of a first part disposable in contact with a cavity defined in said organ and a second part disposable in contact with said exterior surface of said organ, opposite polarities of voltage being applied to said first and second parts of said conductive array.

27. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells, wherein said source of a low voltage, pulsed, DC electric gradient field is a conductive array disposable in contact with a cavity defined in an organ comprised of said biological cells, wherein said conductive array is comprised of a first plurality of electrodes having a first polarity and a second plurality of electrodes having a second polarity, said low voltage, pulsed, DC electric gradient field being established between said first plurality of electrodes and said second plurality of electrodes.

28. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells, wherein said source of a low voltage, pulsed, DC electric gradient field provides a high frequency pulsed DC field applied to said biological cells at a group repetition rate.

29. The apparatus of claim 28 wherein said source of a low voltage, pulsed, DC electric gradient field provides a voltage gradient across said biological cells of 0.1 to 10 V/cm.

30. The apparatus of claim 28 wherein said source of a low voltage, pulsed, DC electric gradient field provides a pulse of DC voltage of approximately 1 ms long at approximately 500 Hz with a 50% duty cycle.

31. The apparatus of claim 28 wherein said source of a low voltage, pulsed, DC electric gradient field provides a burst of pulses of DC voltage followed by a rest period of the order of several seconds.

32. The apparatus of claim 31 wherein said rest period is of the order of 5 seconds.

33. The apparatus of claim 31 wherein said burst of pulses is of the order of 0.1–2 second.

34. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells, wherein said source of a low voltage, pulsed, DC electric gradient field is a conductive array disposable in contact with a cavity defined in an organ comprised of said biological cells, and wherein said conductive array is comprised of a flexible mesh conformable to said cavity.

35. The apparatus of claim 24 further comprising an inflatable balloon disposed within said conductive array.

36. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells, wherein said source of a low voltage, pulsed, DC electric gradient field is a conductive array is a pair of conformed and opposed plates between which said biological cells are disposed such that the plates conform to opposing surfaces of the biological cells.

37. An apparatus for electroporation of biological cells comprising:

a perfusion medium in which said biological cells are disposed;

a source of a low voltage, pulsed, DC electric gradient field established across said biological cells; and a source of genes, proteins, or drugs to be transferred into and then from said perfusion medium into said biological cells, wherein said source of a low voltage, pulsed, DC electric gradient field is a conductive array disposable in contact with a tissue comprised of said biological cells, wherein said tissue defines a lumen, wherein said conductive array is a cylindrical mesh inflatable within said lumen, and wherein said cylindrical mesh is comprised of a plurality of separate electrodes provided in two sets with opposing polarities.

38. An apparatus for electroporation of biological cells comprising:

a perfusion medium in which said biological cells are disposed;

a source of a low voltage, pulsed, DC electric gradient field established across said biological cells for transferring genes, proteins, or drugs from said perfusion medium into said biological cells;

a source of genes, proteins, or drugs to be transferred into and then from said perfusion medium into said biological cells; and wherein said electric gradient field is provided by at least one conductive array of point electrodes conformed to a contour of a surface of tissue that comprises said biological cells in a non-penetrating manner to provide a more even distribution and homogenous strength of said electrical gradient field applied on the tissue.

* * * * *